United States Patent
Gao et al.

(10) Patent No.: US 9,861,664 B2
(45) Date of Patent: Jan. 9, 2018

(54) TRADITIONAL CHINESE MEDICINE COMPLEX COMPOSITE FOR SIGNIFICANTLY IMPROVING HIGH DENSITY LIPOPROTEIN CONCENTRATION IN SERUM AND PREPARATION METHOD THEREOF

(71) Applicants: Zhuangcun Gao, Shandong (CN); Xiangyu Gao, Shangdong (CN)

(72) Inventors: Zhuangcun Gao, Shandong (CN); Xiangyu Gao, Shangdong (CN)

( * ) Notice: Subject to any disclaimer, the term of this patent is extended or adjusted under 35 U.S.C. 154(b) by 107 days.

(21) Appl. No.: 14/771,505

(22) PCT Filed: Jun. 12, 2014

(86) PCT No.: PCT/CN2014/079771
§ 371 (c)(1),
(2) Date: Aug. 31, 2015

(87) PCT Pub. No.: WO2015/027730
PCT Pub. Date: Mar. 5, 2015

(65) Prior Publication Data
US 2016/0008406 A1    Jan. 14, 2016

(30) Foreign Application Priority Data

Aug. 30, 2013   (CN) .......................... 2013 1 0384204

(51) Int. Cl.
| | | |
|---|---|---|
| A61K 36/236 | (2006.01) | |
| A61K 36/734 | (2006.01) | |
| A61K 36/285 | (2006.01) | |
| A61K 35/02 | (2015.01) | |
| A61K 35/34 | (2015.01) | |
| A61K 35/32 | (2015.01) | |
| A61K 35/36 | (2015.01) | |
| A61K 36/23 | (2006.01) | |
| A61K 36/725 | (2006.01) | |
| A61K 9/20 | (2006.01) | |
| A61K 35/35 | (2015.01) | |
| A61K 9/14 | (2006.01) | |

(52) U.S. Cl.
CPC ................ *A61K 35/34* (2013.01); *A61K 9/14* (2013.01); *A61K 9/20* (2013.01); *A61K 9/2095* (2013.01); *A61K 35/32* (2013.01); *A61K 35/35* (2013.01); *A61K 35/36* (2013.01); *A61K 36/23* (2013.01); *A61K 36/236* (2013.01); *A61K 36/285* (2013.01); *A61K 36/725* (2013.01); *A61K 36/734* (2013.01)

(58) Field of Classification Search
CPC .. A61K 36/734; A61K 36/285; A61K 36/236; A61K 35/12
USPC .................................. 424/732, 774, 778, 548
See application file for complete search history.

(56) References Cited

U.S. PATENT DOCUMENTS

2007/0059386 A1* 3/2007 Lee ........................ A61K 36/00
424/725

\* cited by examiner

Primary Examiner — Chris R Tate
Assistant Examiner — Deborah Davis

(57) ABSTRACT

A traditional Chinese medicine complex composite for significantly improving high density lipoprotein (HDL) concentration in serum, includes: a tablet which includes 30%-50% hawthorn from north China, 10%-30% *radix aucklandiae*, 10%-30% *radix glehniae* and 10%-30% *ligusticum wallichii*; and a powder which includes 40%-60% beef, 15%-35% bovine sinew, 15%-35% pigskin and 0.5%-2.5% Chinese-date. The tablet is prepared by decocting and boiling the raw material medicine with water, and the powder is prepared by catalytic hydrolysis with an enzyme, the pigskin in the powder can be replaced with bovine skin or donkey skin, and the bovine sinew can be replaced with bovine tendon.

6 Claims, No Drawings

TRADITIONAL CHINESE MEDICINE COMPLEX COMPOSITE FOR SIGNIFICANTLY IMPROVING HIGH DENSITY LIPOPROTEIN CONCENTRATION IN SERUM AND PREPARATION METHOD THEREOF

CROSS REFERENCE OF RELATED APPLICATION

This is a U.S. National Stage under 35 U.S.C 371 of the International Application PCT/CN2014/079771, filed Jun. 12, 2014, which claims priority under 35 U.S.C. 119(a-d) to CN 201310384204.5 filed Aug. 30, 2013.

BACKGROUND OF THE PRESENT INVENTION

Field of Invention

The present invention relates to the field of preventing and treating heart disease and cerebrovascular disease, and more particularly to a traditional Chinese medicine complex composite for significantly improving high density lipoprotein (HDL) concentration in serum and a preparation method thereof.

Description of Related Arts

High density lipoprotein (HDL) is a serum protein with the smallest particles mainly translated in liver and small intestine. In 1975, the American doctor Miler firstly discovered the anti-atherosclerosis factor HDL and disclosed that hyperlipidemia is not the only cause of coronary heart diseases, decreasing of HDL may be an important or critical aetiological agent of coronary heart disease.

In 1985, American doctors Brown and Goustein disclose metabolic mechanism of HDL in a new perspective as follows. HDL is capable of actuating reverse cholesterol transport, by which the trashes in the blood and the tissue such as cholesterol are carried via reverse transport to the liver for decomposition to be eliminated out of the human body in a reversal direction. Furthermore, HDL has a plurality of beneficial effects such as changing bad effects of endothelium, decreasing platelet aggregation and inhibiting oxidation of LDL (low density lipoprotein). The two doctors are awarded with the Nobel Prize in Medicine due to the outstanding contribution.

In recent years, studies have shown that HDL has the definite effects of anti-atherosclerosis and is capable of "absorbing" cholesterol in the atherosclerosis vascular wall to be transported to the liver for metabolic clearance. It is proved by arteriography that the content of HDL has significantly negative correlation with severity of stenosis of the arterial lumen, thus the HDL has the laudatory title of vascular scavenger. The international medical community clearly realized that whoever improves the HDL, who solves the problem of the coronary heart disease or even the cerebrovascular disease, and thus who can prolong lifespan of the human beings by several decades in theory.

In 2006, a plurality of medical centers from five countries and regions of China, America, England and etc researched improving oral niacin and simvastatin to increase HDL and decrease in serum. The research lasted for 4 years and over thirty thousand patients with coronary heart disease were observed. In the large-sample, random, double-blind research with the comparison of placebo. A plurality of evidences of evidence-based medicine proves that oral niacin and simvastatin does not have satisfying effect on increasing the HDL in blood. Currently, there is not a satisfying medicine capable of improving the HDL in serum. Thus, based on the great treasury of traditional Chinese medicine, it is necessary to take advantage of the traditional Chinese medicines in treating various chronic diseases, so as to discover and research a traditional Chinese medicine complex composite for significantly improving high density lipoprotein (HDL) concentration in serum and a preparation method thereof.

SUMMARY OF THE PRESENT INVENTION

An object of the present invention is to provide a traditional Chinese medicine complex composite for significantly improving high density lipoprotein (HDL) concentration in serum, so as to change the situation of not having a satisfying traditional Chinese medicine available for improving high density lipoprotein (HDL) concentration in serum.

The traditional Chinese medicine complex composite of the present invention comprises Tiaozhong tablet and Jisheng powder.

1. Tiaozhong Tablet

The Tiaozhong tablet comprises: hawthorn from north China, *radix aucklandiae*, *radix glehniae* and *ligusticum wallichii*, wherein weight percentages thereof are: hawthorn from north China 30%-50%, *radix aucklandiae* 10%-30%, *radix glehniae* 10%-30% and *ligusticum wallichii* 10%-30%.

Preferably, weight percentages of the hawthorn from north China, the *radix aucklandiae*, the *radix glehniae* and the *ligusticum wallichii* in the Tiaozhong tablet are: hawthorn from north China 35%-45%, *radix aucklandiae* 15%-25%, *radix glehniae* 15%-25% and *ligusticum wallichii* 15%-25%.

Preferably, weight percentages of compositions in the Tiaozhong tablet are: hawthorn from north China 40%, *radix aucklandiae* 20%, *radix glehniae* 18% and *ligusticum wallichii* 22%.

A main composition of the Tiaozhong tablet is *radix aucklandiae* which has drug properties of pungent, bitter and warm. The *radix aucklandiae* has an effect of regulating and removing stagnancy, reinforcing the spleen to promote digestion and promoting qi circulation and relieving pain. The *radix aucklandiae* serves as monarch drug in a prescription in the Tiaozhong Tablets.

Another important composition in the Tiaozhong tablet is hawthorn from north China which has drug properties of sour, sweet and slightly warm. Studies show that hawthorn from north China is capable of decreasing blood fat, improving blood circulation, preventing transport of calcium ion, assisting stabilizing cardiac muscle, and has the effects of anti-hypertension and anti-atherosclerosis. The hawthorn from north China serves as ministerial drug in the Tiaozhong tablet.

The *ligusticum wallichii* in the Tiaozhong tablet with drug properties of pungent, warm is capable of promoting blood and qi circulation and dispelling wind and relieving pain.

The *radix glehniae* in the Tiaozhong tablet with drug properties of sweet, slightly cold has effects of tonifying stomach, promoting fluid, nourishing fever and causing diuresis. Both the *ligusticum wallichii* and the *radix glehniae* serve as adjuvant.

The Tiaozhong tablet of the present invention has beneficial effects of regulating middle qi, invigorating stomach, rectifying body weak and dyspepsia and recovering normal physiological function of the spleen and stomach, nourishing Yin and promoting circulation and removing stasis. The key of composition of the present invention is to affect a permanent cure. The present invention starts with regulating the effect of spleen and stomach. The therapeutic goal of the present invention is to treat the obstacle in the process of absorbing, digesting and converting substances such as essential amino acid for synthesizing HDL in the human body. The present invention firstly restores the physiological basis of synthesizing satisfying level of HDL, and thus creates a condition for the application of the Jisheng powder and the increase of pharmacological effects thereof, which is the key of significantly improving the HDL concentration in serum.

The preparing method of the Tiaozhong tablet adopts the conventional pharmaceutical techniques of traditional Chinese medicine such as water decoctum and concentration. The drug product prepared comprises tablets, powder, pills, capsula and etc.

2. Jisheng Powder

The Jisheng powder of the present invention comprises: beef, bovine sinew, pigskin and Chinese-date, wherein weight percentages thereof are: beef 40%-60%, bovine sinew 15%-35%, pigskin 15%-35%, Chinese-date 0.5%-2.5%.

Preferably, weight percentages of compositions of the Jisheng powder are: beef 45%-55%, bovine sinew 20%-30%, pigskin 20%-30% and Chinese-date 1%-2%.

Preferably, weight percentages of compositions of the Jisheng powder are: beef 50%, bovine sinew 24%, pigskin 25% and Chinese-date 1%.

A main composition of the Jisheng powder is beef with drug properties of sweet, warm and non-toxic. The beef has effects of regulating the middle-energizer, benefiting vital energy and nourishing the spleen and stomach. Being rich in beef protein, the beef is a main resource for obtaining amino acid and serves as monarch drug in the Jisheng Powder.

A second important composition of the Jisheng powder is pig skin with drug properties of sweet and cool and being rich in collagen. A third important composition of the Jisheng powder is elastin. The elastin has an effect of nourishing yin, increasing osmotic pressure of the blood, decreasing blood viscosity, anticoagulation and improving microcirculation. The pig skin can be replaced by cow leather, donkey skin or skin of other large scale mammal and serves as a ministerial drug in the Jisheng powder.

The bovine sinew which is a large hamstring in the Jisheng powder has drug properties of salty cool and being rich in scleroprotein mainly comprising keratin, collagen, reticulin, elastin and etc and is beneficial to maintain elasticity and healthy of the artery. The bovine sinew can be replaced by bovine tendon, or replaced by sinews (large hamstrings) or tendons of other big scale mammal and serves as adjuvant in the Jisheng powder.

The Chinese-date in the Jisheng powder has properties of sweet, peaceful and non-toxic and has effects of reinforcing spleen, regulating stomach and promoting salivation. The Chinese-date serves as a corrigent in the formula and serves as a conductant drug.

The beef, bovine sinew and pigskin are all flesh and blood products having great effect of Tonifying yin and qi and improving the nutritional status, anti-aging and significantly improving immunity of human body. The Jisheng powder mainly takes temporary solution. The effective constituent of the Jisheng powder is protein hydrolysate which is nutrient agent with main composition of multiple amino acids and is essential substances for synthesizing HDL. The protein hydrolysate is capable of providing enough and efficient multiple amino acids for synthetizing satisfying level of HDL and is substance dependence for significantly improving HDL concentration in serum.

The preparing method of Jisheng powder adopts a process comprising enzyme catalyzed hydrolysis. The medicine is put in a container and added with a defined amount of water and then added with proteolytic enzyme, so as to produce hydrolysate of animal protein via hydrolysis reaction.

In the present invention, the Tiaozhong tablet and the Jisheng powder are combined together for usage, so as to coordinate and supplement each other to significantly increasing concentration of HDL in serum. The combination of the Tiaozhong tablet and the Jisheng powder is suitable for prevention and treatment of diseases such as heart diseases and cerebrovascular disease which are caused by atherosclerosis and for anti-aging as well.

Theoretical effects of the present invention are as follows:

Inner Canon of Huangdi 2000 years ago disclosed that diseases are not born with people, can be caught and treated. If someone says the disease can not be treated, he does not get the skill. In order to follow the old adage, the present invention takes the advantages of traditional Chinese medicine in treating various chronic diseases, explores and develops a traditional Chinese medicine complex composite of Tiaozhong tables and Jisheng powder, so as to solve the difficult medical problems of the reduction of HDL level in serum.

According to the classical theory of Chinese medicine, spleen and stomach is the hinge of lifting and lowering various channel qi. If the spleen channel is lifted, other channels of liver, kidney, triple burner, small intestine and large intestine are all lowered. If the stomach channel is lowered, channels of the liver, kidney, pericardium, gallbladder and bladder are all lowered, in such as manner that the human body is capable of achieving the effects of without stagnation in meridians and with a peaceful qi and blood, in such a manner that the intake nutrient in the human body is capable of being fully digested, absorbed, transported, metabolized, secreted and excreted, which is a physiological basis for synthesizing satisfying level of HDL.

The key point of the Tiaozhong tablet of the present invention is to regulate channels of spleen and stomach, so as to restore the qi of all channels in the human body to a normal and well aligned state, so as to achieve an effect that essential amino acids, nutriments etc., which are required in synthesizing the HDL in a satisfying level are capable of being fully digested, absorbed and converted in a high efficiency. Thus, the Tiaozhong tablets are the basis drugs in significantly improving the HDL concentration in serum.

The nutritional immunology also tells us that the human being has a formidable and sophisticated immune system. Only when the immune system is healthy and strong, can the cancer be recovered like influenza. Except for hereditary disease, almost all the diseases of the human being have something to do with immune reactions. If the immunity of the human body is improved and maintains operating in a normal state, a vast majority of the human beings is hopefully to be cured. The only and must thing people can do is to provide sufficient nutrition for the immune system, so as to recover the immune system and keep the immune system in a healthy and powerful state to be cured even when in a ill status, which is also the secret of healthy and longevity. The theory is consistent with the academic idea in inner Canon of Huangdi that if the human body is in a healthy atmosphere, the evil influence is not capable of invading.

DETAILED DESCRIPTION OF THE PREFERRED EMBODIMENT

Further description of the present invention is illustrated combined with the preferred embodiments.

A traditional Chinese medicine complex composite of the present invention comprises Tiaozhong tablet and Jisheng powder.

I. Tiaozhong Tablet

Example 1

Weigh 5 kilograms of hawthorn from north China, 1.8 kilograms of *radix aucklandiae*, 1.6 kilograms of *radix glehniae* and 1.6 kilograms of *ligusticum wallichii*, set aside.

A preparing method of the Tiaozhong tablet comprises steps of: selecting and mixing four components of the Tiaozhong tablet, flushing with water, weighing out one tenth of total weight of the Tiaozhong tablet for drying and smashing to obtain dry powder, and then processing according to conventional Chinese pharmaceutical manufacturing technology comprising steps of: soaking the four components of the Tiaozhong tablet which is not selected, decocting with water, filtering, concentrating, adding all of the dry powder mentioned above, initially forming solid medicine, drying, crushing to produce powder, and preparing tablets. Each tablet has a weight of 0.3-0.4 g.

Usage: Take orally, 4-6 tablets each time, twice a day.

Preferably, the tablets can also be made into powder, pills or capsule.

Example 2

Weigh 3.5 kilograms of hawthorn from north China, 2.5 kilograms of *radix aucklandiae*, 1.6 kilograms of *radix glehniae* and 2.4 kilograms of *ligusticum wallichii*, set aside.

Preparation and usage methods of this example are identical with those of the example 1.

Example 3

Weigh 4 kilograms of hawthorn from north China, 2 kilograms of *radix aucklandiae*, 1.8 kilograms of *radix glehniae* and 2.2 kilograms of *ligusticum wallichii*, set aside.

Preparation and usage methods of this example are identical with those of the example 1.

II. Jisheng Powder

Example 1

Weigh 6 kilograms of beef, 1.5 kilograms of bovine sinew, 2.3 kilograms of pig skin, 0.2 kilogram of Chinese-date, set aside.

A preparing method of the Jisheng powder comprises: selecting the beef, the bovine sinew, the pigskin and the Chinese-date, washing with water, cutting the beef, the bovine sinew and the pigskin into pieces or strips, boiling for 10-15 min, levigating, feeding water to blend into appropriate paste, then processing by a enzyme catalyzed hydrolysis technology, wherein a process of the enzyme catalyzed hydrolysis technology comprises steps of: adding papain to the paste, processing hydrolysis reaction under 60° C. for 12 hours, boiling 15 min to destroy enzyme, performing high speed centrifugation to degrease, deslagging, filtering to obtain animal protein hydrolysate in a liquid state, concentrating, spray drying, packaging to obtain powder products. Each package has a weigh of 10-15 g.

Usage: Take orally, for an adult, 1 package each time, three times a day. The Jisheng powder can be taken with meals.

Example 2

Weigh 4.5 kilograms of beef, 2.35 kilograms of bovine sinew, 3 kilograms of pig skin, 0.15 kilogram of Chinese-date, set aside.

Preparation and usage methods in this example are identical with those in the example 1.

Example 3

Weigh 5 kilograms of beef, 2.4 kilograms of bovine sinew, 2.5 kilograms of pig skin, 0.1 kilogram of Chinese-date, set aside.

Preparation and usage method is identical with the example 1.

While using, the tablets, powder, pills or capsule obtained in the three examples is combined randomly with powdery products obtained in the three examples of Jisheng powder.

The traditional Chinese medicine complex composite: Tiaozhong tablets and Jisheng powder are capable of significantly improving high density lipoprotein (HDL) concentration in serum, have better effects than western medicine of niacin and statin, and thus is a traditional inartificial Chinese medicine having great potential value.

INDUSTRIAL APPLICABILITY

The Jisheng powder of the present invention contains various kinds of amino acids, which is the main substance for constituting various immune cells, antibodies and complements and the like in the human body. Only when the kinds and the amount of the amino acids are sufficient, can the human body synthesizing various kinds of immune cells, antibodies, complements and etc. The Jisheng powder of the present invention significantly improves the immunity of the human body to keep the immune system healthy and strong, in such a manner that most of the diseases of the human body including reduction of the HDL level of the serum are expected to be cured. In addition, according to the principle of biochemistry, when the human body utilizes amino acids and other substances to synthesize HDL, under the condition of unchanged enzyme concentration and other conditions, improving the concentration of the substrate amino is capable of improving the synthesis speed of HDL. On the condition of having sufficient amino acids, the increase of the product HDL is capable of increasing the HDL concentration in serum. The Jisheng powder is capable of high efficiently and sufficiently providing the required amino acids for synthesizing HDL, which is the substance for significantly improving HDL concentration in serum.

Apparently, the Tiaozhong tablets and the Jisheng powder of the present invention are combined together for application, so as to treat both manifestation and root cause of disease to fully develop the effect of significantly improving HDL concentration in serum.

In a small sample of an experiment lasted for 6 years for utilizing the present invention to improve HDL concentration. The average value of HDL concentration at the beginning of the testee is a base line. After applying the medicine of the present invention for 1 to 6 years, the HDL concentration in serum of the testee has maximum increasing magnitude of 92.6%, and a minimum increasing magnitude of 43.9%. During the 6 years, the median of the HDL in serum has improved for 65.6% than the base line, no apparent side effects and no exception in the liver and kidney. The experiment confirms that the present invention is capable of significantly improving HDL concentration in serum, and the effects thereof are better than the medicine of niacin and statins.

Apparently, the present invention is capable of significantly improving HDL concentration in serum, without apparent side effects and can be applied in long time. Though the medicine of the present invention has slow onset of at least three months, the effects thereof is steady and permanent. In addition, the medicine of the present invention can be applied combining with a statin drug, so as to combine treating and cultivating, and the application thereof is convenient. The medicine of the present invention is natural and has great potential value and expected to be essential drugs for treating cardiovascular and cerebrovascular diseases.

What is claimed is:

1. A combination for improving high density lipoprotein (HDL) concentration in serum, comprising: a Tiaozhong tablet and Jisheng powder;
    wherein the Tiaozhong tablet comprises: hawthorn from north China, radix aucklandiae, radix glehniae, and ligusticum wallichii, wherein the weight percentages of the hawthorn is 30%-50%, the radix aucklandiae is 10%-30%, the radix glehniae is 10%-30% and the ligusticum wallichii is 10%-30%; and
    wherein the Jisheng powder comprises: beef, bovine sinew, pigskin and Chinese-date, wherein the weight percentages of the beef is 40%-60%, the bovine sinew is 15%-35%, the pigskin is 15%-35%, and the Chinese-date is 0.5%-2.5%.

2. The combination according to claim 1, wherein weight percentages of compositions of the Tiaozhong tablet are: hawthorn from north China 35%-45%, radix aucklandiae 15%-25%, radix glehniae 15-25% and ligusticum wallichii 15%-25%;
    wherein the weight percentages of the Jisheng powder are: beef 45%-55%, bovine sinew 20%-30%, pigskin 20%-30% and Chinese-date 1%-2%.

3. The combination according to claim 1, wherein weight percentages of compositions of the Tiaozhong tablet are: hawthorn from north China 40%, radix aucklandiae 20%, radix glehniae 18% and ligusticum wallichii 22%;
    wherein the weight percentages of the Jisheng powder are: beef 50%, bovine sinew 24%, pigskin 25% and Chinese-date 1%.

4. The combination according to claim 1, wherein the pigskin in the Jisheng powder is replaced by cowhide or donkey hide.

5. The combination according to claim 1, wherein the bovine sinew is obtained from cow hoof.

6. A method for treating a heart disease or a cerebrovascular disease which is caused by atherosclerosis in a subject in need thereof comprising administering to the subject an effective amount of the combination according to claim 1.

* * * * *